(12) United States Patent
Kariathungal et al.

(10) Patent No.: US 7,576,757 B2
(45) Date of Patent: Aug. 18, 2009

(54) SYSTEM AND METHOD FOR GENERATING MOST READ IMAGES IN A PACS WORKSTATION

(75) Inventors: Murali Kumaran Kariathungal, Hoffman Estates, IL (US); Prakash Mahesh, Schaumburg, IL (US); Mark Richard, Naperville, IL (US); Weng Lei, Mt. Prospect, IL (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 188 days.

(21) Appl. No.: 11/334,597

(22) Filed: Jan. 18, 2006

(65) Prior Publication Data

US 2006/0139319 A1 Jun. 29, 2006

Related U.S. Application Data

(63) Continuation-in-part of application No. 11/077,299, filed on Mar. 10, 2005, which is a continuation-in-part of application No. 11/039,152, filed on Jan. 19, 2005, now Pat. No. 7,501,995.

(60) Provisional application No. 60/631,045, filed on Nov. 24, 2004.

(51) Int. Cl.
*G09G 5/00* (2006.01)
(52) U.S. Cl. ................ 345/637; 345/619; 345/629; 345/672; 345/676
(58) Field of Classification Search ............ 345/619, 345/629, 637, 672, 676
See application file for complete search history.

(56) References Cited

U.S. PATENT DOCUMENTS

| 6,243,095 | B1 * | 6/2001 | Shile et al. | 715/854 |
|---|---|---|---|---|
| 7,058,901 | B1 * | 6/2006 | Hafey et al. | 345/619 |
| 7,162,623 | B2 * | 1/2007 | Yngvesson | 345/619 |
| 2002/0101436 | A1 * | 8/2002 | Shastri et al. | 345/619 |
| 2006/0146071 | A1 * | 7/2006 | Morita et al. | 345/619 |
| 2006/0155579 | A1 * | 7/2006 | Reid | 705/2 |
| 2006/0181548 | A1 * | 8/2006 | Hafey et al. | 345/619 |
| 2006/0256382 | A1 | 11/2006 | Matraszek et al. | |

OTHER PUBLICATIONS

Weathermon, A. et al., "iScout: An Intelligent Scout for Accessing and Navigating Large Images Sets in a PACS", Journal of Digital Imaging , vol. 17, No. 2, Jun. 2004, pp. 109-119.*
Office Action mailed Oct. 6, 2008 in U.S. Appl. No. 11/077,299.

* cited by examiner

*Primary Examiner*—Chante Harrison
(74) *Attorney, Agent, or Firm*—Hanley, Flight & Zimmerman, LLC

(57) ABSTRACT

Certain embodiments of the present invention provide methods and systems for identification of most read images. Certain embodiments provide automatically determining a reading time for an image based on at least one of image viewing time and tool usage with respect to the image, and generating a viewing order for the image based on the reading time. Reading times may be determined for a plurality of images. In certain embodiments, a priority may be assigned to the image based on the reading time. Images may be arranged on a display based on the priority, for example. A series of images may be ordered according to reading time for each of a plurality of images, for example.

20 Claims, 6 Drawing Sheets

SYSTEM AND METHOD FOR GENERATING MOST READ IMAGES IN A PACS WORKSTATION

RELATED APPLICATIONS

The present application is a continuation-in-part of, and claims priority from, U.S. patent application Ser. No. 11/077,299, filed on Mar. 10, 2005, which claims priority as a continuation-in-part of U.S. patent application Ser. No. 11/039,152, filed Jan. 19, 2005 now U.S. Pat. No. 7,501,995, and entitled "System and Method for Presentation of Enterprise, Clinical, and Decision Support Information Utilizing Eye Tracking Navigation", which claims priority from, U.S. Provisional Application No. 60/631,045, filed on Nov. 24, 2004.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to display of information in a healthcare environment. In particular, the present invention relates to use of visual tracking technology to improve selection and display of significant images in a healthcare environment.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility. Data entry and access is also complicated in a typical healthcare facility.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminate some of the repetitive motion in order to minimize repetitive motion injuries would be highly desirable.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, HIS, RIS, CIS, CVIS, LIS, and/or EMR, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitate operation of an imaging system and related services by an individual operator would be highly desirable.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Hospitals and other healthcare environments currently have many disparate enterprise information systems that are not integrated, networked or in communication with each other. Currently, a practitioner must log on to different systems and search for a patient to retrieve information from the systems on that patient. During a diagnostic interpretation process, when practitioners use a variety of clinical information to make a diagnosis, for example, practitioners must physically locate workstations containing specific information that they are seeking. Practitioners must log-in, navigate to a particular patient, and then "drill down" or locate a specific kernel of information. Practitioners must currently undertake this manual process for each bit of information they are seeking.

For example, a radiologist identifies a mass in a patient's kidney. Before diagnosing, the radiologist is interested in particular lab results, such as PT (blood clotting), Creatinine, Gleason Score, etc. Currently, a radiologist must access different systems to obtain all of the lab results. Thus, the radiologist may be presented with a large amount of information to review. The radiologist then uses a workstation to parse the lab results and identify the specific desired information. The radiologist must then remember the values and interpretation of the values and enter the values and interpretation into his or report. Such a process may be time consuming. Thus, a system and method providing increased integration between systems and information would be highly desirable.

Depending upon vendors and systems used by a practitioner, practitioners, such as radiologists or cardiologists, have only a few options to reference the tools available. First, a request for information from the available tools may be made in paper form. Second, a practitioner may use different applications, such as a RIS, PACS, EMR, HIS, CIS, CVIS, and LIS, to search for patients and examine the information electronically.

In the first case, the practitioner shifts his or her focus away from a reading workstation to search and browse through the paper, which in most cases includes many pieces of paper per patient. This slows down the practitioner and introduces a potential for errors due to the sheer volume of paper. Thus, a system and method that reduce the amount of paper being viewed and arranged by a practitioner would be highly desirable.

In the second case, electronic information systems often do not communicate well across different systems. Therefore, the practitioner must log on to each system separately and search for the patients and exams on each system. Such a tedious task results in significant delays and potential errors. Thus, a system and method that improve communication and interaction between multiple electronic information systems would be highly desirable.

Additionally, even if systems are integrated using mechanisms such as Clinical Context Object Workgroup (CCOW) to provide a practitioner with a uniform patient context in several systems, the practitioner is still provided with too much information to browse through. Too much information from different applications is provided at the same time and slows down the reading and analysis process. There is a need to filter out application components that a user will not need in a routine workflow. Thus, a system and method which manage information provided by multiple systems would be highly desirable.

Additionally, radiologists, cardiologist, or other healthcare practitioners may repeatedly view similar types of exams during a reading or other review. Currently, PACS and other medical information systems lack tools to extract interpretation behavior of healthcare practitioners to customize workflow. That is, workflow, such as a radiology or cardiology workflow, is designed by PACS or other medical information system developers and is not customized for particular practitioners or types of practitioners. The PACS or other system does not adapt to interpretation patterns of the user, such as a radiologist or cardiologist. Thus, a practitioner's efficiency at using a PACS workstation or other system workstation may no improve over time. A system and method that improves customization of workflow for a practitioner would be highly desirable.

One type of interpretation behavior that may be recorded is a length of time that a practitioner, such as a radiologist or cardiologist, views each image in an exam, for example. A practitioner, such as a radiologist or cardiologist, may focus primarily on certain images ("significant images") to perform an analysis. Identification of significant images reduces a number of images a referral physician or other practitioner examines for diagnosis and/or treatment of a patient. Currently, significant images are manually identified by the practitioner from the images viewed in an exam. Thus, there is a need for a system and method to improve selection and display of significant images in a healthcare environment.

Currently, a healthcare environment such as an operating room (OR) includes multiple displays (CRT, LCD, etc.) connected to multiple, disparate information and/or imaging systems. The displays may be hanging on boom mounted arms from walls, ceilings, tables, and/or floors, for example. In some healthcare settings, such as an OR, ten or more displays may clutter the room and cause great difficulty for practitioners trying to locate key information without scanning each display.

When practitioners wish to access information from the disparate systems, the practitioners must currently turn their heads to look up at the multiple displays and determine which display holds the desired information. Head movement, particularly during a medical procedure, is neither ergonomically correct nor comfortable for the practitioner. Additionally, such head movement may be very repetitive throughout an examination or procedure. Thus, a system and method that reduce head movement and improves ergonomics in a healthcare environment would be highly desirable.

In addition, multiple displays results in an overabundance of information presented simultaneously to a healthcare practitioner. Thus, too much information on too many displays creates difficulty for a practitioner attempting to locate relevant information. Therefore, there is a need for a system and method to improve identification of key information and reduce display clutter in a healthcare environment.

Further difficulties may arise from having too many displays in a healthcare environment, such as an OR. For example, multiple displays are not cost effective from an information technology perspective. Purchasing multiple displays for one or more rooms represents a significant expense for a healthcare provider. Additionally, for example, multiple displays and/or multiple systems generate additional heat in a healthcare environment. Excess heat contributes to higher electric bills and may pose a health hazard to patients, practitioners, and equipment in a healthcare environment. Therefore, a system that reduces multiple displays in a healthcare environment would be highly desirable.

Current PACS workstation technologies allow a radiologist to read images of a study by providing image navigation techniques. Once the study is read by the radiologist, the PACS workstations does not currently allow the radiologist to quickly review the images on which the radiologist spent most of the time reading and analyzing. Under normal conditions, radiologists will spend most of their time analyzing images which are clinically relevant.

Thus, there is a need for systems and methods to improve selection and display of significant images in a healthcare environment. Systems and methods allowing radiologists or other users to quickly access images which they spend most of their time reading would be highly desirable. There is a need for systems and methods for generating the most read images in a healthcare environment, such as a PACS.

BRIEF SUMMARY OF THE INVENTION

Certain embodiments of the present invention provide methods and systems for identification of most read images. Certain embodiments provide a method for most read image identification including automatically determining a reading time for an image based on at least one of image viewing time and tool usage with respect to the image, and generating a viewing order for the image based on the reading time. The method may also include automatically determining reading times for a plurality of images. In certain embodiments, the method may further include assigning a priority to the image based on the reading time.

In certain embodiments, images may be arranged on a display based on the priority. A priority may be assigned to the image based on a reading time greater than a threshold, for example. A priority may be assigned to the image based on a predefined number of longest reading times, for example. In certain embodiments, a priority may be assigned to the image based on a comparison of the reading time with at least one of a threshold and a second reading time for a second image.

In certain embodiments, the method further includes creating a series of images ordered according to reading time for each of a plurality of images. In certain embodiment, the series of images is stored. In certain embodiments, the series of images may be referred to another user.

Certain embodiments provide a computer-readable storage medium including a set of instructions for execution on a computing system. The set of instructions includes a reading time routine for automatically determining a reading time for each of a plurality of images based on at least one of image viewing time and tool usage with respect to each of the plurality of images, and an ordering routine for generating a viewing order for the plurality of images based on the reading times for each image. In certain embodiments, the ordering routine generates a viewing order for the plurality of images based on priority, wherein a priority is assigned to each of the plurality of images based at least in part on reading time. In certain embodiments, the ordering routine saves a series of images according to the viewing order. In certain embodiments, the ordering routine is configured to order a second plurality of images based on the viewing order for the plurality of images. In certain embodiments, the ordering routine arranges the plurality of images for display based on the reading time.

Certain embodiments provide a system for identification of most read images. The system includes a tracking module configured to automatically track reading time for an image based on image display, tool usage, and image viewing, and a processor for associating a reading time with an image. The processor determines a viewing order for the image based on the reading time.

In certain embodiments, the tracking module tracks reading times for one or more users, and the processor determines viewing orders for one or more users. In certain embodiments, the tracking module tracks reading times for a plurality of images. In certain embodiments, the system further includes a data store for storing the image viewing order. In certain embodiments, meta-data associated with the image identifies a priority associated with the image based on the reading time.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Image review and analysis may be a significant component of a healthcare workflow. For example, in a radiology reading, a radiologist spends a significant portion of his or her time reading and analyzing clinically relevant images. Clinically relevant images are the images that may be used for diagnosing a patient's medical condition, for example. In order to read images, a radiologist may use a variety of tools, such as window level, zoom/pan, rotate, image filter(s), process, cine, annotate, etc. For example, a user may dynamically modify a display window level to read images. Different window level settings may allow a user to better view an image or anatomy within an image, for example. A user may zoom and/or pan images for details, for example. A user may rotate and/or flip an image, for example. A user may apply one or more filters to an image to read specific areas of a body part or anatomy of interest. A user may apply image processing tools to image data, for example. Using cine, a user may navigate images quickly, for example. Additionally, a user may annotate image(s) to indicate findings, priority, and/or other note(s), for example. These and other tools may be applied to one or more images for reading.

Time spent reading an image may be determined by analyzing tools applied to the image. For example, time spent within a tool may be measured with respect to an image, and/or a number of tools used with respect to an image may be measured. For example, an operating system or other hardware, software or firmware may be used to track when a tool operation starts and when the operation ends to determine time spent with respect to an image. Additionally, time spent may be determined by measuring an amount of time the image is visible on a display. Furthermore, a user's gaze may be tracked to measure an amount of time spent viewing an image.

A clock counter or other hardware device or software routine serving as a time tracking module may track reading time and/or tool usage, for example. In certain embodiments, time information may be aggregated from one or more measurements. Reading time information may be used to order or arrange images in a study or series to allow a user to more quickly access the most read images in a study/series. Reading time information may be used to associate a priority with one or more images for display.

In an embodiment, a new series may be constructed to store read time information in a PACS for easier access. Images in a most read image series may be ordered based on an amount of time spent by a user reading the images, for example. In an embodiment, an image with a largest time spent reading is assigned a high priority for display, such as display on a PACS workstation. In an embodiment, one or more images may be arranged on a display based on priority.

In an embodiment, a reading order may be stored in a separate data table, image file header, data structure, etc. In an embodiment, an image table may be modified to include an entry for image reading order. In an embodiment, a flag or other data field associated with each image may be included in a header or data table/structure for reading order and/or significance of the image.

Figure 1:
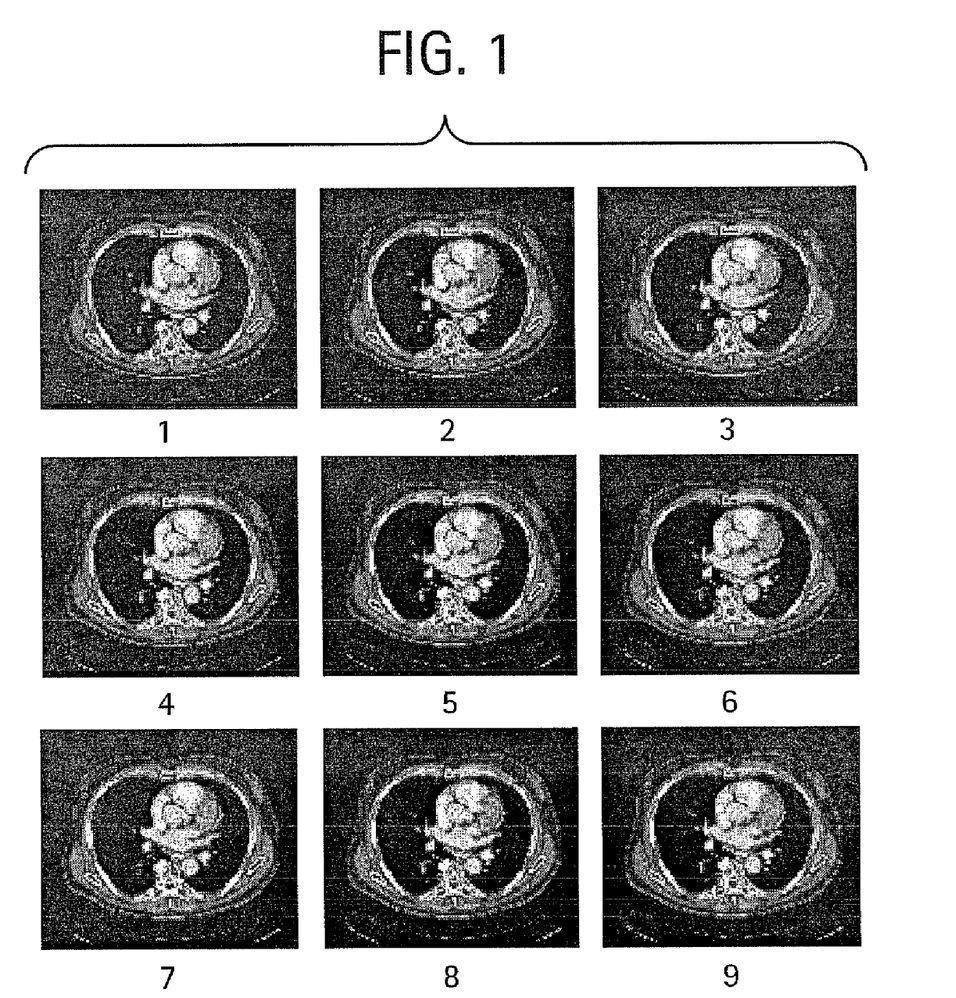
FIG. 1 depicts an exemplary series of images reviewed by a radiologist.
Figure 2:
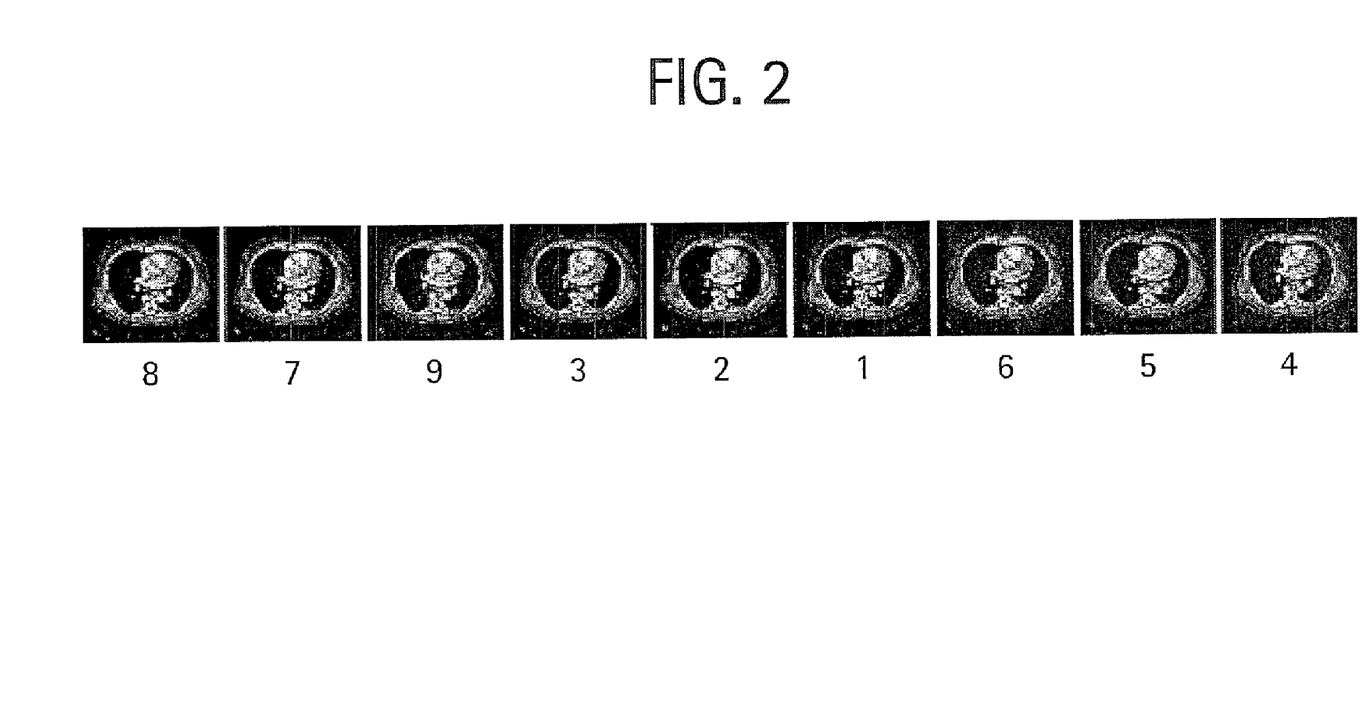
FIG. 2 illustrates a series of images created based on level of image significance in accordance with an embodiment of the present invention.

FIG. 1 depicts an exemplary series of images reviewed by a radiologist. As an example, the radiologist spends most of the time reading images in the following order: 8,7,9,3,2,1,6, 5,4. As shown in FIG. 2, a series of images may be created based on the image reading order. In this example (FIG. 2), image 8; will receive the highest priority, based on the amount of time spend reading the image.

In an embodiment, a reading order in an image study may be matched to the reading order of a previous image study. For example, images in a new study may be registered with images in a previous study, and images in the new study may be displayed according to an order of corresponding images in the previous study.

Thus, certain embodiments provide access to and display of clinically relevant images of a historical study. Certain embodiments provide access to and display of clinically relevant images of a current study while image reading is in progress. Certain embodiments allow ordering and/or prioritization of images based on the amount of time spent reading each image.

In certain embodiments, a new series of images may be created based on priority order for future access. A series may be automatically generated based on reading time. Images in a series may be ordered based on reading time. Image may be prioritized based on reading time. Certain embodiments provide quick access to most read images of a historical and/or current study.

Figure 3:
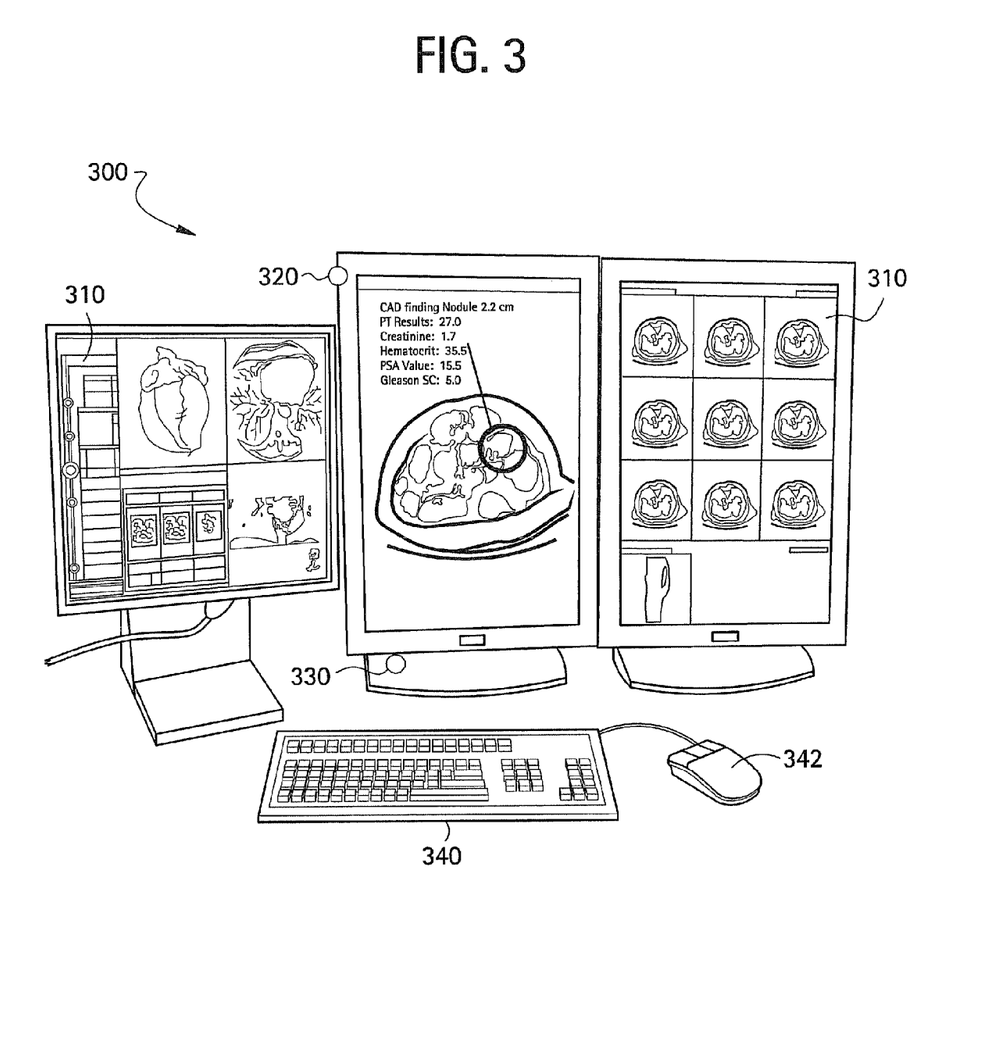
FIG. 3 illustrates an improved display system for selecting and displaying information in accordance with an embodiment of the present invention.

FIG. 3 illustrates an improved display system 300 for selecting and displaying information in accordance with an embodiment of the present invention. The system 300 includes a display 310, a tracking device 320, microphone 330, and manual input devices 340, 342. The components of the system 300 may communicate via wired, wireless and/or infrared communication, for example. The components of the system 300 may be implemented separately and/or integrated in various forms, for example.

As shown in FIG. 3, one or more simple display devices 310 may be used to display information to a user. The display 310 may be used with a camera and/or a portable eyewear and eye tracking system, such as a gaze or visual tracking system including the tracking device 320, to display information for one or more users. By tracking where a user is focusing or fixating his or her visual attention, an accurate measure of user intent may be inferred. Eye or gaze tracking may be faster and more efficient than a mechanical pointing or selecting device, such as a keyboard 340 or mouse 342.

Additionally, voice commands and/or gesture control using cameras, such as fire-wire web cams, may allow interaction with imaging and information systems without disrupting a sterile field. The tracking device 320 may be used in conjunction with gesture control, for example. The microphone 330 may be used in conjunction with voice or subvocal command and control, for example.

The tracking device 320 may be a camera, for example. The tracking device 320 may work instead of and/or in conjunction with a headset or eyewear worn by a user, for example (not shown). The tracking device 320 may be attached to the display device 310, such as on a side or top of the display device 310.

A visual or gaze tracking system may be based on a camera system (e.g., visible light or infrared), for example, and may be active or passive. Alternatively or in addition, a user's gaze may be tracked based on movement of the user's head via a camera or position sensor, for example. Multiple cameras may be used to track a location of a user's gaze. Additionally, multiple cameras may be used to drive a cursor or other indicator on a display, such as the display device 310. The gaze tracking system may include head gear, such as goggles or other ocular device, for a user to wear and/or may use a display-mounted camera or sensor, for example. In an embodiment, the gaze tracking system is calibrated for a user. By tracking a user's gaze, a system may initiate communication, selection, and/or function at a remote system, for example.

Figure 4:
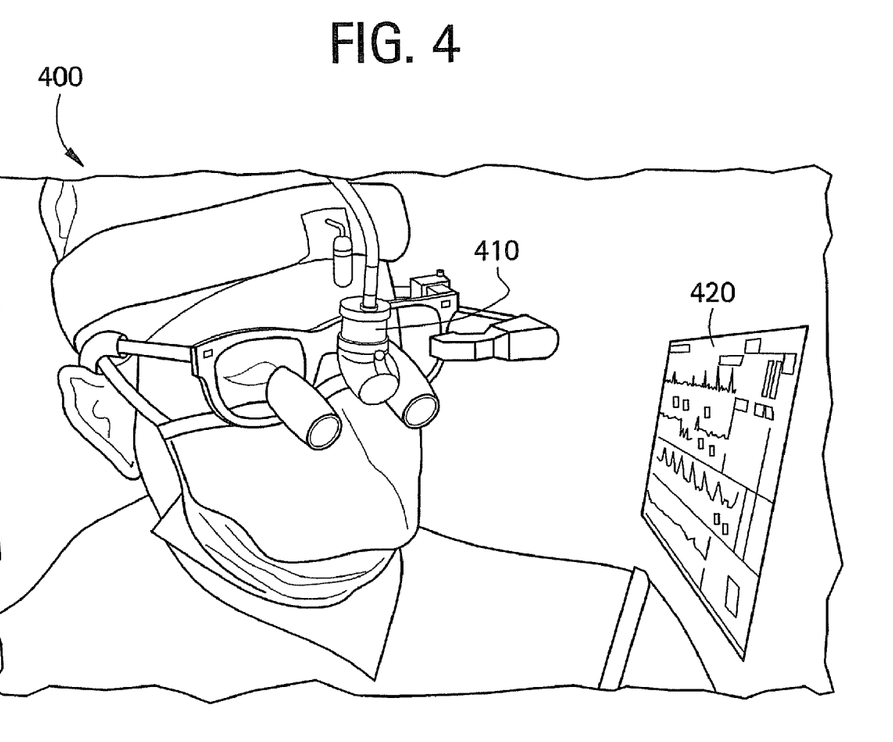
FIG. 4 depicts a portable eyewear viewing system used in accordance with an embodiment of the present invention.

FIG. 4 depicts a portable eyewear viewing system 400 used in accordance with an embodiment of the present invention. The system 400 includes an eyewear headset 410, a personal eyewear display 420, and a gaze tracking processor 430. The processor 430 may be integrated into the eyewear 410 and/or separate from the eyewear 410. The personal eyewear display 420 is projected in a user's field of view by the eyewear 410.

A healthcare practitioner may use eyewear 410, such as goggles, to capture the practitioner's gaze and perform interface navigation. A user's gaze may be tracked via infrared or other light source, for example. Light may be reflected off of the user's pupil(s) and detected. Light may also be reflected off of the front and rear surfaces of the cornea(s) and lenses of the user's eye(s) and detected or recorded. Repeated measurements track a change in the user's gaze. Alternatively or in addition, a user's gaze may be tracked based on movement of the user's head via a camera or position sensor, for example. A position of the user's gaze and/or head in a reference coordinate system and/or with respect to a reference point, such as a location on a display, may be determined. In an embodiment, a plurality of measurements may be obtained to determine a user's line of sight and/or head angle, for example.

In an embodiment, goggles or other eyewear may also project images into a user's oculars or provide a miniature screen attached to the eyewear 410 and positioned in the user's field of vision to form a virtual personal display 420.

Thus, eyewear 410 may be used to eliminate some displays in the healthcare environment. Additionally, eyewear 410 may allow specific information to be targeted for display for specific users in the healthcare environment. For example, a nurse, an anesthesiologist, and a surgeon receive different information displayed on their personal eyewear display 420. For example, a surgeon may view image-guided surgery and PACS data while an anesthesiologist views EKG and dosage data. In an embodiment, each user may view customized information without turning to look at a display to select the information.

In an embodiment, the eyewear 410 is a portable eyewear viewer that displays key dynamic patient information such as hemodynamic data, cardiology waveforms, vital signs, etc. Eyewear 410 allows a user to view information without turning his or her head to view an LCD or CRT monitor. Although the eyewear headset 410 allows users to view data while working "heads down" on a patient, resolution may be limited for image review and/or fine text review, for example. When a user wishes to view detailed information or a finer degree of granularity, the user may look at a larger display device in the healthcare environment.

An eye or gaze tracking capability of the headset 410 and/or processor 430 may be used to control a display device, such as the display device 310. For example, the processor 430 detects when a user is looking at a certain button, option or feature on a display and selects or activates the button, option or feature for the user. Activation of an option/feature may also be based on an amount of time a user is looking/has looked at a certain area. The eyewear system 400 may also be used in conjunction with voice commands and/or gestures to control the display device 310 and/or other systems or features, for example.

In an embodiment, a user looks at the display device 310. The gaze tracking processor 430 recognizes that the user wants to see certain information and displays context-sensitive information for the patient on the display device 310, for example. Information on gaze and/or head position may be relayed from the processor 430 to determine information on the display device 310. Additionally, user preference information, information from the display device 310, and/or other input may be transmitted to configure the contents and/or other parameters of the display device 310.

In an embodiment, information displayed on the display device 310 may be determined based on rules and/or perspectives, for example. For example, rules determine that a doctor's gaze takes precedence over a nurse's gaze. Then, when the doctor turns away from the display device 310, the nurse gains control of the display device 310. Alternatively, control of the display device 310 may be shared by multiple users and common information displayed on display device 310 so that multiple users may be accommodated at approximately the same time.

The processor 430 and/or other processor or system related to the display device 310 may have an ability to arbitrate conflicts and priority among a plurality of users seeking access determine which user(s) should take control of the display device 310. For example, rules-based display control and/or hanging protocols may govern which user has control and priority and/or which users may share control and display area. Rules and other protocols may also govern when control over the display device 310 is relinquished and/or preempted.

In an embodiment, video switchboxes and/or voice commands may be used with image-guided surgery to switch displays so that only image-guided surgery information is viewed. In an embodiment, voice control and/or gestures may be used in conjunction with eye tracking to control the display device 310 and/or a system cursor.

In an embodiment, a user, such as a radiologist, may review images via the display device 310. The user may identify one or more of the images as significant images. In an embodiment, access to significant images may be streamlined or shortcut. For example, a user may access one or more significant images with a single click of a mouse button or other simple selection to reduce a user's effort in locating significant images when reviewing an exam or collection of images. A medical information system, such as a PACS system, may store significant image information to enable simplified retrieval of significant images by a user.

A visual tracking system, such as the tracking system 320 and/or the viewing system 400, may be integrated into an information system, such as a PACS workstation, and/or work in conjunction with an information system to track an amount of time a user, such as a radiologist, spends viewing each image in an exam or collection, for example. The visual tracking system may be used to track a location at the display device 310 at which the user is looking. Based on location and duration information, the information system, such as a PACS, may present images to the user, such as a radiologist, in a more efficient manner.

In an embodiment, one or more significant and/or most read images for a user may be selected automatically based on the length of time an image has been viewed by the user. For example, the images viewed for longer than a certain time period are automatically selected as significant and/or most read images. The time period may be selected by a user, administrator, system parameter, and/or experimental data, for example. Alternatively, a system may be configured to store a certain number (n) of significant and/or most read images for a user. The n images viewed for the longest period of time by the user are then denoted as significant and/or most read images, for example. Viewing times may be stored as meta-data, for example, associated with each image. In another embodiment, most recently viewed images may be stored for a user. For example, the n most recently viewed images and/or images viewed within a certain time period may be stored for a user or group of users.

For example, for a CT abdominal pelvis exam, images in the top five percent of viewing durations are automatically selected as significant and/or most read images. For example, a PACS server stores viewing or dwell times for a radiologist for an exam including 6 images based on gaze or other visual tracking. The viewing times are 1390 ms for image 1, 3908 ms for image 2, 1970 ms for image 3, 9077 ms for image 4, 9660 ms for image 5, and 3433 ms for image 6. Images 4 and 5 are selected as significant and/or most read images based on the viewing times.

The significant and/or most read images may be flagged using meta-data stored in or with the images or denoted in a table or database, for example. In an embodiment, a user may be alerted to the detection and storage of significant and/or most read images. The user may review the selected significant and/or most read images and modify significant and/or most read image designation if desired. Significant and/or most read image identification may occur automatically and/or may be triggered by a user via software or other electronic trigger, for example. In an embodiment, gaze-based significant and/or most read image selection may be augmented by and/or work in conjunction with voice command and mousing device input, for example. In an embodiment, significant and/or most read images and/or a report, such as a radiology report, may be transmitted automatically or by a user to another practitioner, such as a specialist or referral physician, for review.

A visual tracking system, such as the tracking system 320 and/or the viewing system 400, may be used to track user dwell or gaze time for images on display device 310. The visual tracking system may be a separate system or may be integrated with a PACS or other medical system, for example. In an embodiment, user dwell time is measured when the user is looking at an image. The visual tracking system does not track dwell time when the user is looking at text, buttons, or other peripheral content, for example. The tracking system tracks a user's gaze in relation to the display device 310. The user's gaze location on the display device 310 may be mapped to content displayed at display device 310. The system may determine at which content the user is looking. The visual tracking system or other processor or software may compare image dwell times to determine significant and/or most read images based on criteria, such as a minimum time threshold, a minimum and/or maximum number of images, etc.

In an embodiment, rather than manually positioning a cursor over an image or part of an image using a mousing device or keyboard, for example, a visual or gaze tracking system may be used to indicate a location on the display device 310. That is, a visual tracking system, such as one using the tracking device 320, may determine a focus of the user's gaze. The tracking system may also determine a "dwell time" or length of time that the user focuses on a location. If a user focuses on a location for at least a certain period of time, the tracking system may position a cursor at that location on the display device 310, for example. The tracking system may also activate a function with respect to the location and/or retrieve information based on the location, for example. In an embodiment, gazing at a certain location for a certain length of time generates a "roll-over" or overlay of supporting information at the display device 310. For example, if a radiologist is gazing at an image of a kidney, a roll-over is displayed to provide supporting information to allow the radiologist to better understand the case.

In an embodiment, a display area of the display device 310 is mapped with respect to a coordinate system, such as an x-y coordinate system. Areas in an image are mapped to x,y coordinates or other location information, for example. Mapping allows the system to determine what area of an image corresponds to the location of a user's gaze or cursor, for example. Then, the system may store and/or retrieve information related to the area in the image and/or on the display 310. The display device 310 and tracking system may be calibrated to map specific locations in specific types of exam studies, such as modality, body part, etc.

In an embodiment, the visual tracking system and display device may work together with a rules-based context manager to filter and display information. One example of a rules-based context manager is described in U.S. patent application Ser. No. 10/956,171, filed on Oct. 1, 2004, entitled "System and Method for Rules-Based Context Management in Radiology and Cardiology Diagnostic Reading", with inventors Prakash Mahesh, Mark M. Morita, and Thomas A. Gentles, which is herein incorporated by reference in its entirety.

In an embodiment, the visual tracking system and display device may work with a perspectives management system for handling multiple applications and workflow. The perspectives management system allows various perspectives to be defined which save workflow steps and other information for a particular user. Perspectives allow a personalized information display to present relevant information germane to a patient's current condition, for example. One example of a perspectives management system is described in U.S. patent application Ser. No. 10/956,434, filed on Oct. 1, 2004, entitled "System and Method for Handling Multiple Radiology Applications and Workflows", with inventors Prakash Mahesh and Mark Ricard, which is herein incorporated by reference in its entirety. For example, in a surgical OR there may be numerous healthcare practitioners at an OR table who use specific perspectives or views of relevant patient information. With a single, large format display (e.g., an LCD, plasma display, 46" display, etc.), each user has the ability to view their personal perspectives on the display in large and/or small format. The display may be shared among the users.

In an embodiment, the visual tracking system may work in conjunction with one or more systems, such as diagnostic review workstations. Diagnostic review workstations may be used to access enterprise clinical information, for example. For example, a radiologist may access clinical information relevant to a current exam in a "just in time" fashion. One example of a diagnostic review or support system is described in U.S. patent application Ser. No. 11/039,152, filed on Jan. 19, 2005, entitled "System and Method for Presentation of Enterprise, Clinical, and Decision Support Information Utilizing Eye Tracking Technology", with inventors Mark M. Morita, Prakash Mahesh, and Thomas A. Gentles, which is herein incorporated by reference in its entirety. For example, the visual tracking system may be used in conjunction with a decision support or information retrieval system to provide additional resources and capabilities for a user.

Figure 5:
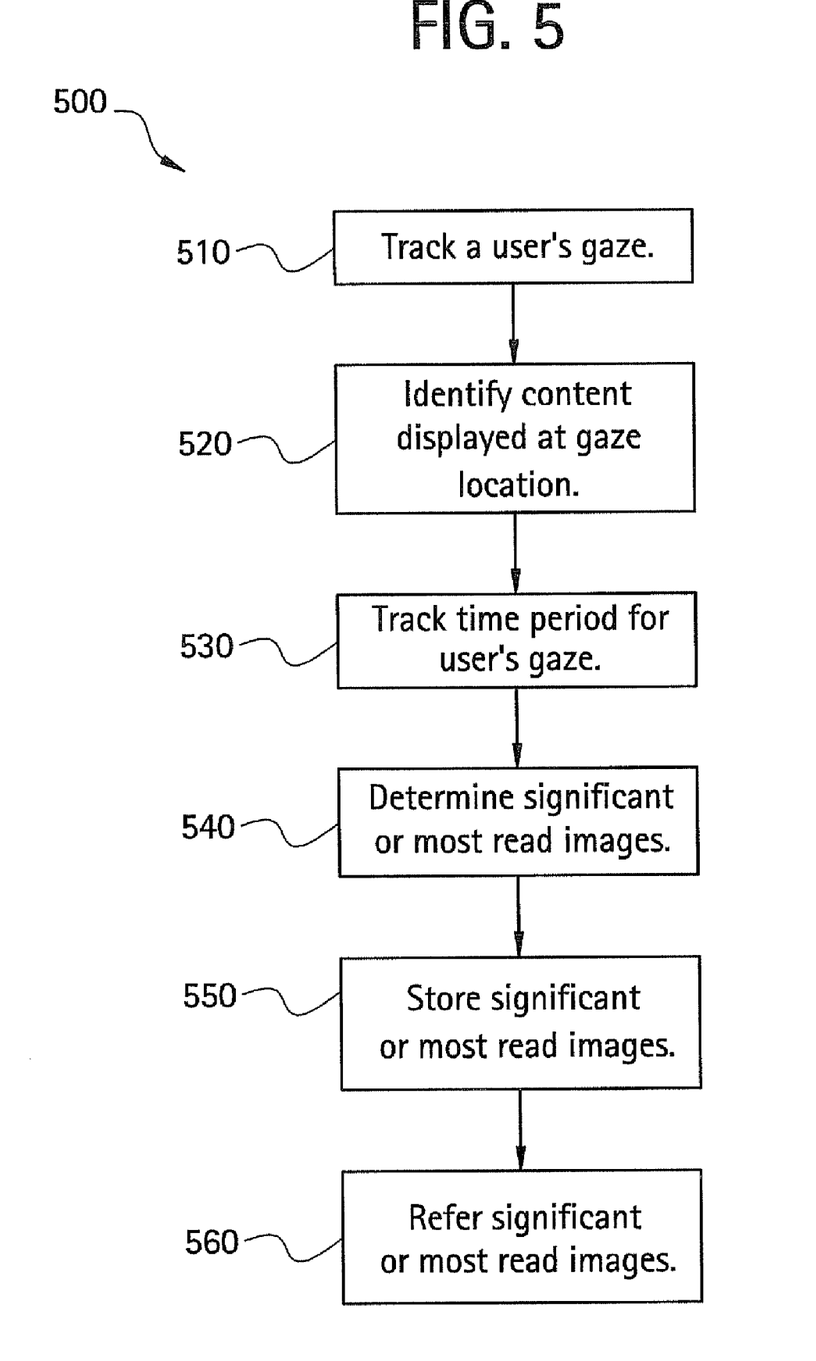
FIG. 5 shows a flow diagram for a method for significant or most read image selection using visual tracking in accordance with an embodiment of the present invention.

FIG. 5 shows a flow diagram for a method 500 for significant or most read image selection using visual tracking in accordance with an embodiment of the present invention. First, at step 510, a user's gaze is tracked. For example, the user's gaze may be tracked via eyewear and/or camera(s). The user's gaze may be tracked in relation to a display device to determine an area on the display device at which the user is looking.

Then, at step 520, content displayed at the location at which the user is gazing is identified. For example, if the user is looking at an image of a chest scan on a display screen, the chest scan image is identified. Next, at step 530, a time period during which the user focuses on an image is tracked. The time period, such as a number of seconds, may be stored as meta-data integrated with or associated with the image, for example. Alternatively or in addition, the time period may be stored in a file, table or database associated with the image.

At step 540, significant or most read images are determined. For example, dwell time periods are compared to determine the most viewed and/or longest viewed images. The images with the largest dwell times may be designated as significant or most read images, for example.

Then, at step 550, significant and/or most read images may be stored. For example, significant or most read images may be stored in a database or other data storage or memory. Alternatively or in addition, meta-data or other data associated with the significant or most read images may be modified to designate the images as significant or most read images, for example.

Next, at step 560, significant or most read images may be referred. For example, a radiologist may refer the significant or most read images to a specialist for review. In an embodiment, a practitioner may automate a referral once significant or most read images are identified.

In an embodiment, a user may modify visual tracking system parameters and/or significant or most read image designations. In an embodiment, a visual tracking system may authenticate a user prior to tracking viewing time and identifying significant and/or most read images. In an embodiment, a visual tracking system may arbitrate between a plurality of users viewing a display device. Viewing and/or access times used to identify significant and/or most read images may be collected from a single user or from a plurality or group of users, for example.

Figure 6:
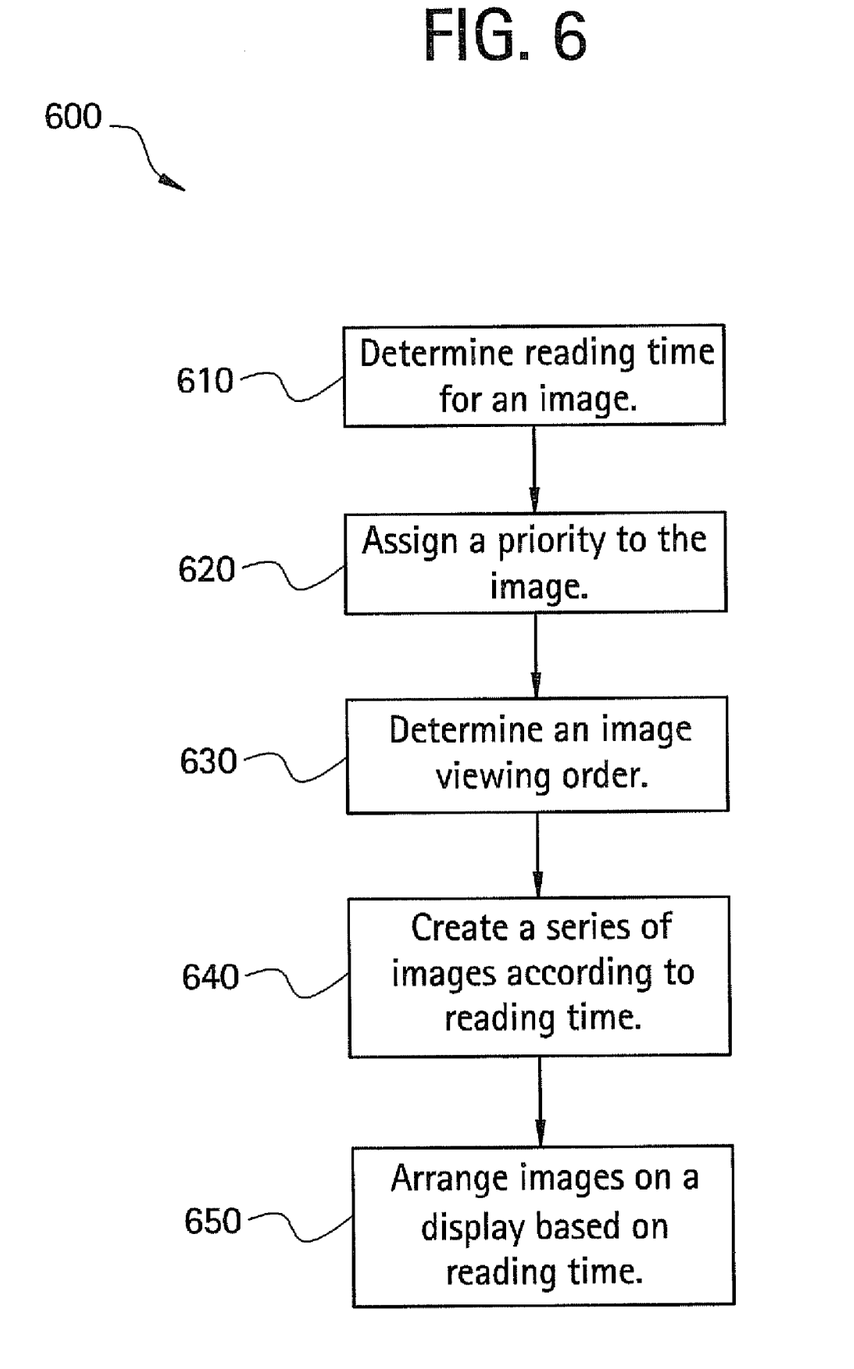
FIG. 6 shows a flow diagram for a method for most read image selection in accordance with an embodiment of the present invention.

FIG. 6 shows a flow diagram for a method 600 for most read image selection in accordance with an embodiment of the present invention. First, at step 610, reading time for an image is determined. Reading time may be determined by gaze tracking, image and/or image processing tool access time, and/or number of processing applications applied to an image, for example. Reading time may be determined by tracking an amount of time that an image is visible on a display. Then, at step 620, a priority is assigned to an image based on the reading time. For example, images one through nine shown in FIG. 1 may be assigned a relative priority based on their respective reading times. Alternatively, one or more images may be assigned an equivalent priority based on a range of reading times (e.g., most read images=9, often read images=3, seldom read images=1).

Next, at step 630, a viewing order for the image may be determined based on the reading time. For example, the series of images in FIG. 1 may be arranged in a certain viewing order as in FIG. 2 based on reading time or priority. At step 640, a series of images may be created according to reading time for each of one or more images. At step 650, one or more images are arranged on a display based on priority and/or reading time. For example, an image with high priority may be displayed prominently on a display, while image(s) with lesser priority are arranged around the high priority image on the display.

Many of the steps of the method 600 may be performed in a variety of orders. For example, step 630 may occur prior to step 620. Additionally, some steps of the method 600 may be omitted. For example, steps 620 or 630 may be omitted. A series of images may be displayed without creating a new series of re-ordered images, for example. The images may be prioritized without arranging the images on a display based on priority, for example.

For example, FIG. 1 shows a set of images acquired for a CT study, which is displayed in the order in which the images were acquired. A user, such as a radiologist, may first open the study in stack mode, for example. The radiologist selects a cine tool to cine or move through the images, which results in a certain amount of time spent viewing the images. Table 1; depicts an example of viewing times for images in the study.

TABLE 1

| Image | Time spent on image |
|---|---|
| Image 1 | 100 ms |
| Image 2 | 100 ms |
| Image 3 | 100 ms |
| Image 4 | 100 ms |
| Image 5 | 100 ms |
| Image 6 | 100 ms |
| Image 7 | 100 ms |
| Image 8 | 100 ms |
| Image 9 | 100 ms |

While cine-ing, the radiologist determines that Image 8, for example, should be reviewed in more detail. The radiologist then uses tools, such as zoom, window level and magnifying glass, on Image 8.

TABLE 2

| Image | Time spent on image |
|---|---|
| Image 1 | 100 ms |
| Image 2 | 100 ms |
| Image 3 | 100 ms |
| Image 4 | 100 ms |
| Image 5 | 100 ms |
| Image 6 | 100 ms |
| Image 7 | 100 ms |
| Image 8 | 200 ms |
| Image 9 | 100 ms |

As shown in Table 2, the image reading time for Image 8; has increased due to tool usage with respect to Image 8. Upon review of Image 8, the radiologist also notices that Images 7; and 9, which as adjacent to Image 8, also merit further detailed review with tools, such as zoom, window level and magnifying glass. Table 3; depicts a change in reading times based on tool usage, for example.

TABLE 3

| Image | Time spent on image |
|---|---|
| Image 1 | 100 ms |
| Image 2 | 100 ms |
| Image 3 | 100 ms |
| Image 4 | 100 ms |
| Image 5 | 100 ms |
| Image 6 | 100 ms |
| Image 7 | 170 ms |
| Image 8 | 200 ms |
| Image 9 | 160 ms |

Continuing review similar to the review described above, for example, may result in different image reading times as shown in Table 4.

TABLE 3

| Image | Time spent on image |
|---|---|
| Image 1 | 120 ms |
| Image 2 | 130 ms |
| Image 3 | 150 ms |
| Image 4 | 100 ms |
| Image 5 | 110 ms |
| Image 6 | 115 ms |
| Image 7 | 180 ms |
| Image 8 | 200 ms |
| Image 9 | 170 ms |

Based on the reading times shown, for example, in Table 4, images in the study of FIG. 1 are reordered. FIG. 2 illustrates the reordered image study, for example.

Thus, certain embodiments help facilitate efficient identification of and access to images important or significant to a healthcare practitioner's diagnosis and/or treatment of a patient. Certain embodiments help increase radiologist and other practitioner productivity by extracting information regarding image interpretation behavior. Certain embodiments present extracted information to the practitioner to allow the practitioner to review an exam or collection of images more efficiently during a subsequent viewing. Additionally, significant and/or most read images may be automatically selected rather than manually indicated. Certain embodiments correlate an amount of time spent viewing an image with designation of the image as a significant and/or most read image. Certain embodiments store viewing time as meta-data for an image. Certain embodiments provide a visual tracking system used for medical image review.

Furthermore, repetitive head and neck movements may be reduced by minimizing use of traditional manual input devices resulting in a reduction in ergonomic difficulties and stress disorders. Wireless and minimally invasive product design allows easy-to-use, comfortable interaction. Thus, certain embodiments allow users to naturally interact with image(s), interface(s) and/or other information on which they are focused.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for most read image identification based on a total time an individual image is viewed, said method comprising:
   automatically determining, using a computer, a total reading time for an individual image based on an image total viewing time of said individual image and tool usage with respect to said individual image, wherein said tool usage is determined by measuring at least one of time spent in a tool with respect to said individual image and a number of tools used with respect to said individual image when reading said image; and
   generating a viewing order for said individual image based on said total reading time; and
   facilitating display of said individual image according to said viewing order.

2. The method of claim 1, further comprising automatically determining said total reading times based on said total time said individual image is viewed for a plurality of images.

3. The method of claim 1, further comprising assigning a priority to said individual image based on said total reading time.

4. The method of claim 3, further comprising arranging said individual images on a display based on said priority.

5. The method of claim 3, wherein said assigning step further comprises assigning a priority to said individual image based on said total reading time greater than a threshold.

6. The method of claim 3, wherein said assigning step further comprises assigning a priority to said individual image based on a predefined number of longest said total reading times.

7. The method of claim 3, wherein said assigning step further comprises assigning a priority to said individual image based on a comparison of said total reading time said individual image is viewed with at least one of a threshold and a second total reading time for a second individual image, said second total reading time of said second individual image based on a viewing time of said second individual image.

8. The method of claim 1, further comprising creating a series of images ordered according to said total reading time based on said total time said individual image is viewed for each of a plurality of images.

9. The method of claim 8, further comprising storing said series of images.

10. The method of claim 8, further comprising referring said series of images.

11. A computer-readable storage medium including a set of instructions for execution on a computing system, the set of instructions comprising:

a total reading time routine for automatically determining a total reading time based on a total time an individual image is viewed for each of a plurality of images based on said total image viewing time and tool usage with respect to each of said plurality of images, wherein said tool usage is determined by measuring at least one of time spent in a tool with respect to said individual image and a number of tools used with respect to said individual image when reading said image; and an ordering routine for generating a viewing order for said plurality of images based on said total reading times that said individual image is viewed for each image.

12. The computer-readable storage medium of claim 11, wherein said ordering routine generates a viewing order for said plurality of images based on priority, wherein a priority is assigned to each of said plurality of images based at least in part on said total reading time.

13. The computer-readable storage medium of claim 11, wherein said ordering routine saves a series0 of images according to said viewing order.

14. The computer-readable storage medium of claim 11, wherein said ordering routine is configured to order a second plurality of images based on said viewing order for said plurality of images.

15. The computer-readable storage medium of claim 11, wherein said ordering routine arranges said plurality of images for display based on said total reading time based on said total time an individual image is viewed.

16. A system for identification of most read images based on a total time an individual image is viewed, said system comprising:

a tracking module configured to automatically track said total reading time for said individual image based on image display time, tool usage, and image viewing time, wherein said tool usage is determined by measuring at least one of time spent in a tool with respect to said individual image and a number of tools used with respect to said individual image when reading said image; and a processor for associating said total reading time with said individual image, said processor determining a viewing order for said individual image based on said total reading time.

17. The system of claim 16, wherein said tracking module tracks said total reading times for one or more users and said processor determines viewing orders for one or more users.

18. The system of claim 16, wherein said tracking module tracks said total reading times for a plurality of images.

19. The system of claim 16, further comprising a data store for storing said individual image viewing order.

20. The system of claim 16, further comprising meta-data associated with said individual image, wherein said meta-data identifies a priority associated with said individual image based on said total reading time.

* * * * *

UNITED STATES PATENT AND TRADEMARK OFFICE
CERTIFICATE OF CORRECTION

PATENT NO. : 7,576,757 B2  
APPLICATION NO. : 11/334597  
DATED : August 18, 2009  
INVENTOR(S) : Kariathungal et al.

Page 1 of 1

It is certified that error appears in the above-identified patent and that said Letters Patent is hereby corrected as shown below:

Column 17, line 33 (Claim 13): should read -- wherein said ordering routine saves a series of images --.

Signed and Sealed this

Third Day of November, 2009

David J. Kappos  
*Director of the United States Patent and Trademark Office*